United States Patent [19]

Nottingham et al.

[11] Patent Number: 4,964,295
[45] Date of Patent: Oct. 23, 1990

[54] BORE MAPPING AND SURFACE TIME MEASUREMENT SYSTEM

[75] Inventors: Lawrence D. Nottingham, Charlotte, N.C.; Thomas E. Michaels; Jennifer E. Michaels, both of Freeville, N.Y.

[73] Assignee: Westinghouse Electric Co., Pittsburgh, Pa.

[21] Appl. No.: 878,649

[22] Filed: Jun. 26, 1986

[51] Int. Cl.$^5$ ............................................ G01N 29/00
[52] U.S. Cl. ................................................. 73/1 DV
[58] Field of Search ............. 73/1 DV, 622, 623, 597, 73/865.8; 367/13, 118, 124, 126, 129; 356/241

[56] References Cited

U.S. PATENT DOCUMENTS

| | | |
|---|---|---|
| 3,221,544 | 12/1965 | Gunkel . |
| 3,415,110 | 12/1968 | Cowan . |
| 3,575,044 | 4/1971 | Gibbs . |
| 3,599,478 | 8/1971 | Weinbaum . |
| 4,008,603 | 2/1977 | Paulissen . |
| 4,393,711 | 7/1983 | Lapides . |
| 4,579,294 | 7/1986 | Brill et al. ............................ 73/623 |

FOREIGN PATENT DOCUMENTS

| | | |
|---|---|---|
| 0139317 | 2/1985 | European Pat. Off. . |
| 664763 | 1/1952 | United Kingdom . |
| 1075461 | 7/1967 | United Kingdom . |

OTHER PUBLICATIONS

H. S. Brooks, A. W. Brown, A. C. Rankin; "Ultrasonic Inspect. of the Nimrod Power Plant Alternator Rotors"; Proc. of the 4th Int'l. Conf. on Non-Destructive Testing; London, Sep. 9-13, 1963; pp. 196-202.

G. J. Posakony; "Ultrasonic Tech. for Remote Inspect. of Nuclear Reactor Vessels"; Periodic Inspect. of Pressure Vessels Conf.; London; May 9-11, 1972; IME, pp. 119-125.

J. N. Baez, C. Venturino, O. Wartman; "In-Service Inspect. Sys. for the 1st Arg. Atomic Power Plant"; Per. Inspect. of Press. Vessels Conf.; London; May 9-11, 1972; IME; pp. 97-101.

SWRI Proj. 17-3286-01 Fin. Rep., V. I.; "Jan. 1972 Inserv. Exam. of San Onofre Nuc. Gen. Stat., Unit 1"; So. Calif. Edison Co.; Apr. 1972, pp. 1-32; A-1—B-5.

"San Onofre Nuc. Gen. Stat. Unit 1 Anal. of 2nd Surveillance Mater. Capsule"; So. Calif. Edison Co.; Jul. 1972, pp. 1-15.

"Jan. 1972 San Onofre Nuc. Gen. Stat. Unit 1 Nondestructive Inserv. Inspect.", So. Calif. Edison Co., Jul. 1972, pp. 1-21.

"In-Serv. Inspect. Tool for Nuc. Reactor Vess."; H. W. Keller, D. C. Burns, T. R. Murray; Conf. on Per. In-
(List continued on next page.)

Primary Examiner—Robert Raevis

[57] ABSTRACT

The present invention includes a bore mapping system that includes one or more high resolution ultrasonic mapping transducers that are used to measure the diameter of a bore. The travel time for a normally incident pulse to reach the bore surface and return for each transducer is used with a reference reflection time measured in a calibration bore to determine the measured diameter from a mechanically measured reference diameter using a known velocity of the ultrasonic pulse in an immersion fluid. The diameter measured by each of the transducers is averaged to obtain an average measured diameter which is produced for plural axial rotor positions. The present invention also includes a surface time measurement system that uses at least one ranging transducer measuring the ranging time required for a ranging beam to reach and return from the bore surface. The measured ranging time is used with a calibrated ranging time obtained in the calibration bore to modify a calibrated inspection beam surface time for an inspection transducer to obtain a current inspection beam surface time. The ranging time can also be used to obtain a correction time curve that provides correction time for the inspection beam surface time versus circumferential bore position. The calibrated inspection beam surface time or the correction time curve, are used to correct positions of flaws in the rotor material.

9 Claims, 6 Drawing Sheets

OTHER PUBLICATIONS spect. of Press. Vess.; London; May 9–11, 1972; IME, pp. 126–139.

"Mech. Equip. for Inserv. Inspect. of Nuc. Reac."; C. E. Lautzenheiser; Conf. Per. Inspect. of Press. Vess.; London; May 9–11, 1972; IME; pp. 205–220.

"Boresonic Inspect. of Forged Turbine & Gen. Rotors"; W. R. Marklein, R. E. Warnow; ASMEP 65–WA/PWR-2; ASMEWA Meeting, N.Y., 11/29–12/4, 1964.

"Inserv. Inspect. of San Onofre Nuc. Gener. Stat. Unit 1,2,3"; C. G. Johnson, D. Albertstein, O. J. Ortega, C. E. Lautzenheiser; ASMEP 70-WA/NE-5; ASMEWA Mtg., N.Y., 11-29 to 12-3, 1970.

"Rev. of the Tech. of Inserv. Inspect."; C. E. Lautzenheiser, III, Inter-American Conf., Feb. 1972.

BORE MAPPING AND SURFACE TIME MEASUREMENT SYSTEM

CROSS REFERENCES TO RELATED APPLICATIONS

This application is related to concurrently filed U.S. applications assigned to Westinghouse and entitled BORESONIC INSPECTION SYSTEM by the inventors of the invention described herein and having U.S. Pat. No. 4,757,716 and entitled ULTRASONIC SIGNAL PROCESSING SYSTEM INCLUDING A FLAW GATE by the inventors of the invention described herein and having U.S. Pat. No. 4,803,638. The above-mentioned applications are incorporated by reference herein.

BACKGROUND OF THE INVENTION

The present invention is directed to a bore mapping and surface time measurement system for a bore hole in a material such as metal and, more particularly, the present invention is directed to a bore mapping system which maps the diameter of a power generating plant turbine rotor bore and measures the time required for an ultrasonic wave to reach the bore surface for later use to correct the transit time of an angled beam refracted by the bore surface to create a shear mode interrogation beam during a shear mode ultrasonic bore inspection.

Power generating station turbines and generator rotors have variable diameter boreholes extending along their central axis over part or all of their lengths. Because the rotors experience the highest stress within approximately the first four inches in rotor radius, the detection of major near bore flaws and the monitoring of flaw location as well as size determinations are of critical importance in determining rotor life expectancy. As a result, at the end of the manufacturing process and during periodic routine rotor maintenance, the bores are inspected for flaws and occasionally remachined over all or part of their surface to remove the flaws. To accurately perform the inspection, the precise geometry in the bore of a particular rotor must be determined. Prior to a rotor inspection, the inside diameter of the bore, as a function of axial position along the bore, needs to be determined to allow inspection transducers to be properly calibrated and manipulated during the inspection.

One method of obtaining bore diameter information is to manually insert a mechanical measurement device into the bore and record the diameter at discrete locations along the length of the bore. One such mechanical measurement device is called a "Star Gauge". The "Star Gauge" measures diameter by mechanically positioning arms inside the bore. The mechanical system suffers from drawbacks related to limited axial resolution and inevitable human error associated with gauge positioning. In addition, such mechanical measuring devices are difficult to align on bore slopes and tapers.

The ultrasonic inspection of the rotor bore involves transporting an ultrasonic transducer through the bore and consists of a combination of circumferential rotation and axial displacement allowing the ultrasonic beam to pass through all of the material of interest. In an immersion type system, the inspection transducer does not contact the bore surface but operates at a distance from the bore. An immersion fluid, such as treated water, provides the necessary sound transmission medium between the transducer and the rotor material. During each rotation and/or axial movement of the transducer and its scan head, the path length travelled by the ultrasonic wave between the transducer and the bore surface can vary due to several factors: (1) the wobble, run-out, or eccentricity of the scan head relative to the bore surface; (2) twisting of the scan head used to transport the transducer; and (3) misalignment of the entire scan head upon entry into the bore.

The location of detected reflectors (flaws) in the rotor material are determined by calculation based on a measured ultrasonic wave propagation or travel time from the transducer to the flaw and back, transducer location at the time of flaw detection and a knowledge of the geometry of the ultrasonic beam path. The propagation velocities of the ultrasonic wave or pulse in the liquid coupling medium and the rotor material are different and the actual path of any wave is composed of a water path component and a metal path component. Only the total time is available as a measurement, thus, the water path component must be precisely known in order to determine the metal path component. It is from the metal path component that the depth of the flaw from the bore surface is calculated. Reference or calibration blocks or bores containing known size reflectors of known geometry at known locations, can be scanned prior to rotor inspection to calibrate the transducers by a procedure in which the geometry of the ultrasonic path is determined to thereby establish the relationship between the inspection transducers and later discovered flaws. If the path length and corresponding surface time of the ultrasonic pulse during an inspection have changed from the path length and surface time measured during calibration, and this change has not been accounted for, the location of the flaws in the rotor material will be incorrectly determined. In extreme cases, reflections originating from within the material can be interpreted as air bubbles trapped in the immersion fluid, or bubbles in the immersion fluid can be interpreted as surface or subsurface reflections from material discontinuities or flaws in the rotor itself. This problem is of particular significance when the ultrasonic beam is not normally incident to the bore surface, as is the case for shear mode inspections.

During a normally incident compressional mode inspection, the ultrasonic beam is directed at the bore surface in a perpendicular or nearly perpendicular direction and produces a strong surface reflection back to the transducer, and the signal from this return echo can be used to locate the surface of the bore from which flaw positions can be measured. In shear mode testing, however, the shear wave is produced by directing a compressional wave in the immersion fluid toward the bore surface at an angle relative to the radial direction, that is, the compressional wave strikes the bore surface at an angle other than perpendicular. This angle is normally about 21° so that a refracted shear wave is created in the rotor material at an angle of about 45° to the surface tangent at the pulse contact point. At this angle of incidence, the surface echo is reflected away from the transducer incident beam path. Thus, no signal is returned to the transducer, and the water path component of the inspection beam cannot be determined from transducers used for shear wave inspection.

Prior art immersion based ultrasonic inspection systems employ a type of bore riding immersion transducer which is mounted in a housing which itself is kept in contact with the bore thereby maintaining the transducers at fixed offsets with respect to the bore surface. The drawbacks of this prior art system are based on two contradictory requirements for a bore riding transducer. The transducer housing must be compliant radially so that the housing properly tracks variations in the bore and yet the support mechanism must be rigid enough so that the compliance does not lead to positional errors.

If the surface time at which the shear mode ultrasonic beam contacts the bore surface is known as a function of circumferential position, the position reporting errors which can occur in a shear transducer inspection system mentioned above, can be corrected if required. Accurate surface time information can also be used to eliminate confusion regarding the source of near bore reflectors or flaws located just inside the bore surface. The first order correction assumes that the geometry of the ultrasonic beam path inside the rotor material has not changed since calibration, and that the change in surface time is due wholly to a change in coupling fluid path length. In practice, the first order correction is the most important for properly locating flaws near the rotor bore surface. Higher order corrections of the refracted beam path can also be performed if the correct surface time is known as a function of circumferential position.

SUMMARY OF THE INVENTION

It is an object of the present invention to provide a system which will rapidly map the inner diameter of a rotor bore.

It is also an object of the present invention to provide a system which will allow high resolution mapping of rotor bore diameter.

It is another object of the present invention to provide a system which will allow surface time correction for the time taken for an ultrasonic longitudinal energy wave to contact a bore surface by striking at an appropriate angle to generate a shear beam in the rotor.

It is still another object of the present invention to provide a surface time correction system which will allow compensation for diameter and alignment variations during rotor inspection.

Some of the above objects can be attained by a bore mapping system that includes one or more high resolution ultrasonic mapping transducers that are used to measure the diameter of a bore. A measured reflection time is used with a reference reflection time to determine the measured diameter from a reference diameter. The diameter measured by the multiple transducers is averaged to obtain an average measured diameter and the average measured diameter is determined at different bore axial positions, thereby mapping rotor diameter axially.

The remaining objects can be attained by a surface time measurement system that uses at least one ranging transducer to measure the ranging time required for a ranging beam to reach the bore surface. The measured ranging time is used with a calibrated ranging time to modify a calibrated inspection beam surface time to produce an inspection beam surface time. The measured ranging time can also be used to obtain a correction time curve that provides a correction time for inspection beam surface time versus circumferential bore position. The calibrated inspection beam surface time or the correction time curve, can be used to correct positions of flaws in the rotor material.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
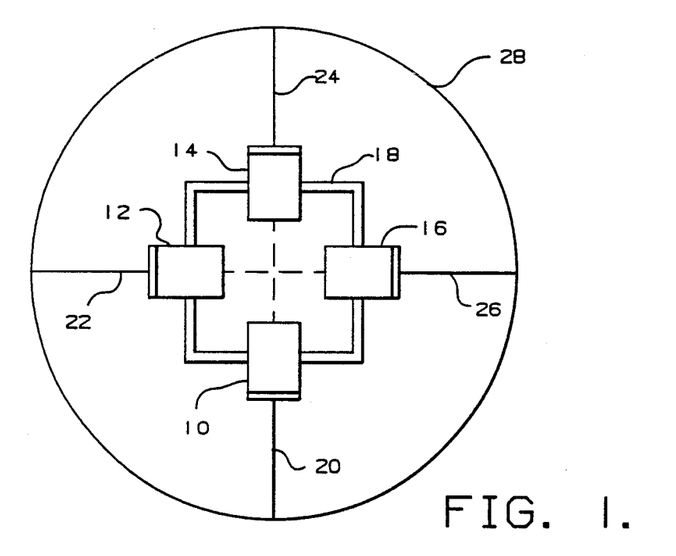
FIG. 1 depicts bore mapping transducers positioned in a rotor bore.

The present invention is directed to a bore mapping system that uses at least one and preferably several ultrasonic transducers 10, 12, 14 and 16, as illustrated in FIG. 1, to measure the diameter of a rotor bore as a function of axial position in the bore. Each transducer is held by a fixture 18 such that the ultrasonic beams 20, 22, 24 and 26 are substantially normally incident upon or perpendicular to the bore surface 28. The bore is preferably filled with a fluid, such as water, that couples the ultrasonic waves from the transducers 10, 12, 14 and 16 to the bore surface 28. As an alternate, a squirting stream of fluid or a fluid-filled cavity can be used to provide the coupling medium between the transducers 10, 12, 14 and 16 and the bore surface 28. Ultrasonic transducers with an active element size of 0.124 to 0.25 inches operating at a frequency from 5 MHz to 10 MHz will be suitable for the mapping function. Such transducers can be obtained from Panametrics of Massachusetts and the preferred model is the V110 transducer. A scan head which transports the transducers 10, 12, 14 and 16 during mapping is discussed as to its details of construction and operation in the related patent mentioned in the cross-references section and entitled BORESONIC INSPECTION SYSTEM.

Figure 2:
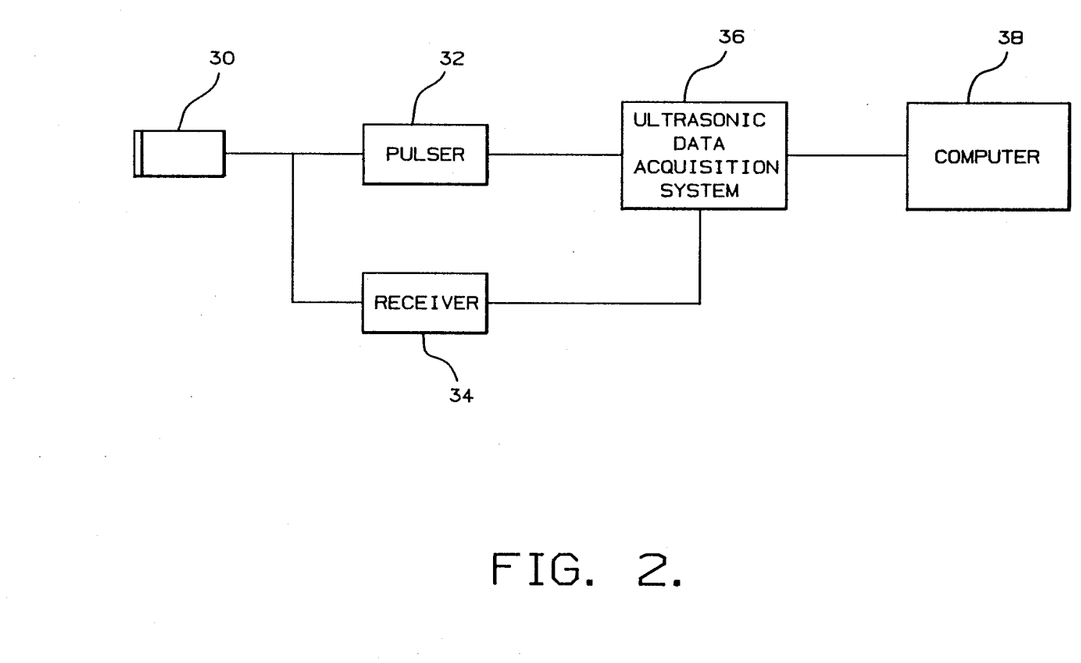
FIG. 2 illustrates the components of the system used to determine bore diameter.

Each transducer 30, as illustrated in FIG. 2, is connected to a pulser circuit 32 which drives the transducer 30 and a receiver circuit 34 which receives the electrical signal created by the ultrasonic reflection from the bore surface 28. The pulser circuit 32 and receiver circuit 34 are controlled by an ultrasonic data acquisition system 36 which is controlled by a computer 38. The computer 38 performs the calculations necessary to obtain the measured bore diameter. The electronic components illustrated in FIG. 2, are discussed as to their details of construction and operation in the related patent mentioned in the cross references section and entitled ULTRASONIC SIGNAL PROCESSING SYSTEM INCLUDING A FLAW GATE. The bore diameter is obtained from the difference between the time of the transmitted pulse and the time of the received echo from the bore surface.

The bore mapping system is calibrated by inserting the transducer assembly of FIG. 1, attached to the front of the scan head, into a cylindrical calibration bore of a known diameter. The calibration or reference bore can be a machined block of a known diameter or could be the end of a rotor bore to be inspected if an accurate diameter measurement of the rotor bore can be made by another method such as by using mechanical calipers.

The transducers are inserted into the calibration bore and rotated in the plus circumferential direction for 360°. During the motion, data are collected from each transducer at increments of approximately 1.4°. The data points are the times $T_i$ for the ultrasonic pulses to travel from the transducer to the bore surface and back. For each transducer, a time $T_{cal}$ is calculated which is the average time over all of the circumferential positions, $$T_{cal} = \frac{1}{N} \sum_{i=1}^{N} T_i. \quad (1)$$

The transducer assembly is rotated in the plus direction while data are being collected to ensure that the mechanical linkage for positioning the transducers is under the same types of stress as when bore mapping occurs.

In the preferred method for obtaining the diameter in the rotor bore to be inspected and mapped, the surface reflection time, at a fixed circumferential position, is obtained for each transducer and a diameter is calculated for each transducer. The diameters are then used to calculate an average diameter value. By averaging, variations due to poor alignment of the transducer assembly inside the rotor bore do not affect the diameter measured.

To map the bore, the transducer assembly is inserted into the bore such that the ultrasonic waves from the transducers 10-16 are substantially normally incident or perpendicular to the bore surface at the axial position of measurement. The diameter reading is obtained by measuring the ultrasonic travel time $T_s$ and computing the diameter D as follows:

$$D = D_{cal} + V(T_s - T_{cal}) \quad (2)$$

In equation (1), $D_{cal}$ is the known diameter of the calibration bore, $T_{cal}$ is the ultrasonic travel time in the calibration bore for the particular transducer obtained during calibration and V is the known velocity of sound in a coupling or immersion fluid corrected for changes in composition and temperature. Water including anti-corrosion inhibitors is an appropriate immersion fluid. The final diameter is obtained by averaging the values from all transducers.

Figure 3A:
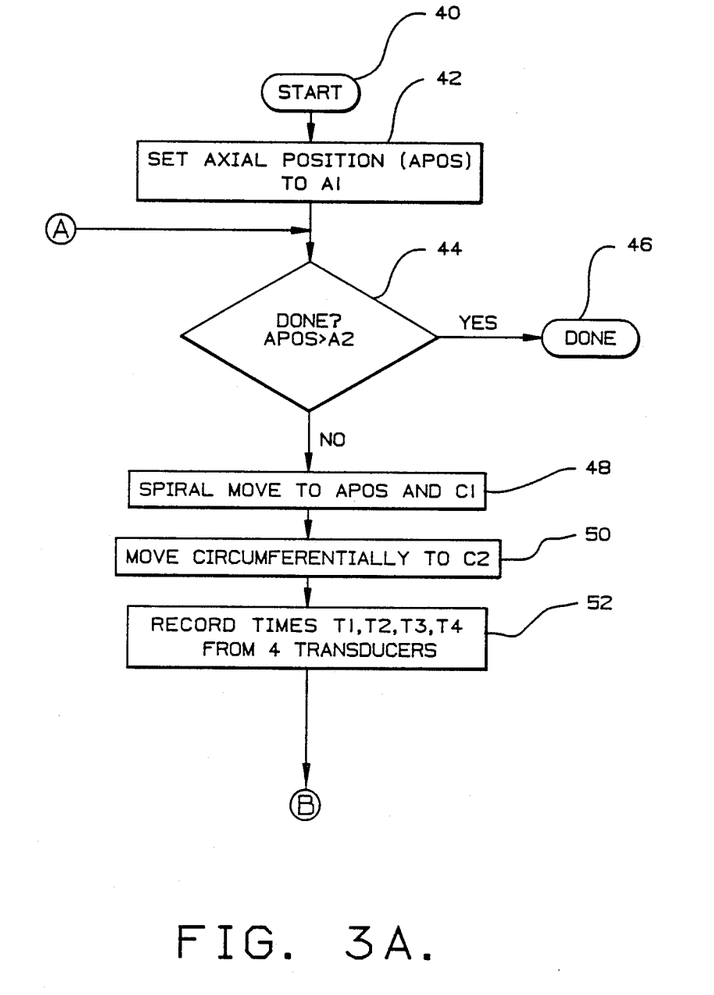
FIGS. 3A and 3B are a flowchart of the procedure performed to map the diameter of a bore.
Figure 3B:
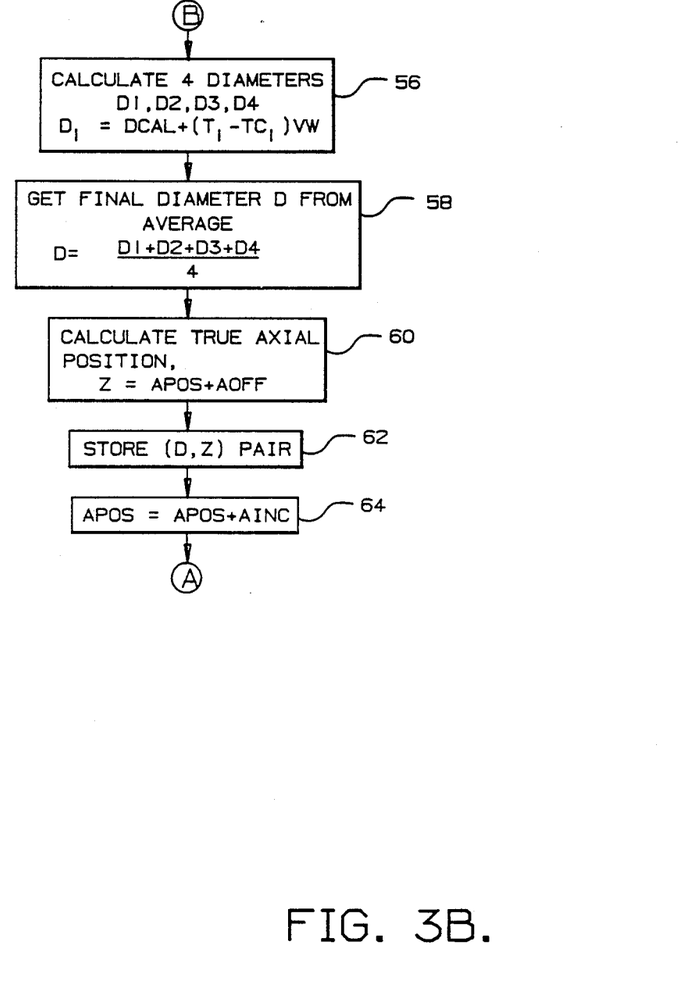

The procedure for mapping the interior of the bore starts by moving the bore mapping transducer assembly of FIG. 1 to a starting axial position A1 as illustrated in FIG. 3. The z axis will be used during this discussion to indicate the bore axial axis and APOS indicates the current axial position along the z axis. After positioning at the starting position A1, procedural control is maintained within a recursive loop until the end position A2 is reached; that is, the mapping procedure for the inner diameter of the bore is completed 46 when the stopping position A2 is less than the current position APOS. After the end of mapping check 44 is completed, a spiral move 48 is performed to move the transducer assembly from a circumferential and axial position at which the most recent measurement has been made to a different circumferential and axial position. A spiral move is preferred, but not the only possibility available, to prevent damage to the rotor by scan head chucks sliding axially along the bore surface. At the end of the spiral move, the transducer assembly is rotated 50 circumferentially to a second circumferential position C2 which is greater than C1 such that circumferential motion from C1 to C2 is in the plus direction. This circumferential rotation ensures that mechanical slack in the scan head mechanism is constant between measurements and the same as during calibration. At circumferential position C2, the surface reflection times for the four transducers 10-16 of FIG. 1 are recorded 52. The reflection times are used to calculate 56 the diameters $D_i$ measured by the four transducers, using the corrected water velocity VW, the calibrated diameter DCAL and the calibrated travel time, $TC_i$, after which the measured diameter D is obtained by averaging 58. Once the average diameter is obtained the true axial position Z of the rotor assembly is calculated by adding an axial offset AOFF to the current axial position APOS. The axial offset AOFF can be the distance between a reference position and the beginning of the rotor bore or the start position A1. Once the true axial position Z is calculated, the average measured diameter D and the true axial position are stored 62 for later reference. Once the diameter D at the current true axial position is stored, the axial position APOS is updated for the next measurement by incrementing with an axial increment AINC. The axial increment AINC determines the axial resolution of the diameter measurement and can be as small as the diameter of the mapping transducer beam; however, an appropriate increment for mapping the typical rotor is approximately one-half inch.

The bore diameter is typically recorded while the scan head carrying inspection transducers is being moved into the rotor bore in the one-half inch increments with a higher resolution (smaller increment) in the axial direction being used whenever bore diameter transition regions are encountered. The bore diameter information is used to control scan head centering devices as the scan head is moved axially along the bore during bore mapping, during insertion and during the ultrasonic inspection as the scan head is retracted from the rotor. The bore diameter transducers are, thus, necessarily the first transducers entering the bore. The bore diameters are generally plotted so that bore zones at which scan head chuck diameters are to be changed can be located to allow the scan head to be held in proper alignment as diameter transition regions are transited.

Figure 4:
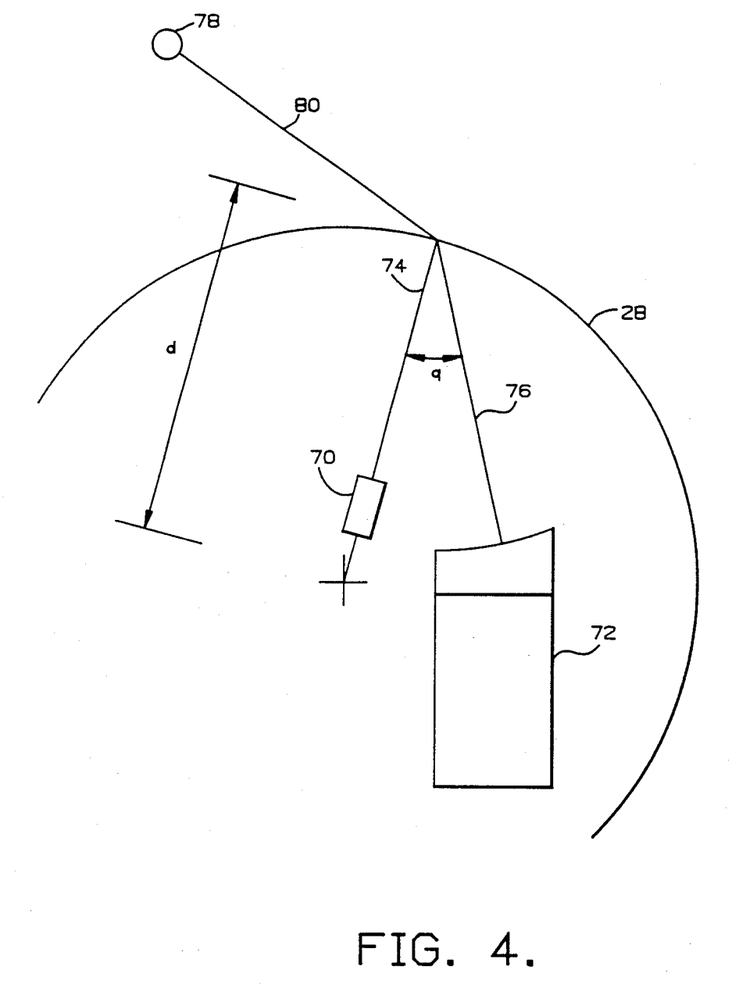
FIG. 4 depicts circumferential transducer position in a surface time measurement system.

During a shear mode ultrasonic inspection of a rotor bore, a radially offset ultrasonic transducer is moved circumferentially inside the bore. The transducer is radially offset such that the beam inside the bore is in a radial-circumferential plane and is not normally incident to the bore surface. When the transducers are operated in a liquid coupling medium rather than in contact with the bore, a critical factor in the calculations for determining the reported depth and location of detected flaws, is the accuracy of the time required for the ultrasonic wave to travel from the transducer to the bore surface and back. During the shear mode inspection in which the interrogating beam in the rotor is propagating in shear mode, the ultrasonic wave, emitted by the radially offset inspection transducer, strikes the bore at an angle relative to the tangent at the point of incidence. Any energy reflected from the bore cannot be detected by the inspection transducer so the surface time cannot be directly measured. The present invention solves this problem by providing a ranging transducer 70 at a known geometric distance from a inspection transducer 72, as illustrated in FIG. 4. The ranging transducer 70 is used to measure the surface time of the inspection transducer 72 ultrasonic wave by measuring the reflection time for the ranging transducer pulse and the water path transit time for the inspection transducer wave is calculated from the known geometric relationship. As the surface time changes due to changes in bore diameter, the location of defects in the rotor detected by the inspection transducer 72, can be adjusted for changes in the surface time due to changes in diameter and the resulting alignment variations that occur during the inspection. The specific way in which the surface time changes are used to correct flaw location is described in the related patent entitled BORESONIC INSPECTION SYSTEM.

The ranging transducer 70 is a flat or non-focussed compressional transducer identical to the bore mapping transducers previously discussed while the inspection transducer is a focused beam device. The inspection transducer is designed to operate in shear mode and to produce a beam diameter of approximately 0.04 inches in the rotor with a focal depth of approximately one inch from the bore surface. Such focussed transducers are obtainable from several vendors with the preferred transducer being available form New York Institute of Technology. The ranging transducer 70 is located as close as possible axially to the inspection transducer 72 and points in a radial direction creating a beam 74 which is normal to the bore surface 28. The ultrasonic beam 74 produced by the ranging transducer 70, must hit the surface of the bore at substantially the same circumferential position as the beam 76 from the inspection transducer 72 so that surface time corrections will be accurate. The electronic components used to perform the calculations discussed herein are depicted in FIG. 2.

To make a surface time correction, a ranging beam surface time during calibration in a calibration bore, which is the time for the ultrasonic wave to travel from the ranging transducer 70 to the bore surface 28 and back, along with an inspection beam surface time during calibration, which is the time for the ultrasonic wave 76 to travel from the inspection transducer 72 to the bore surface 28 and back, must be known. The calibration ranging beam surface time can be directly measured by bouncing an ultrasonic pulse off the calibration bore surface and measuring the time between pulse generation and pulse receipt. The calibration inspection beam surface time cannot be measured directly and must be obtained by extrapolation from travel times measured for reflectors at known positions in a calibration bore and extrapolating back to the surface to get the surface time.

Inspection beam calibration is performed by inserting the transducer configuration of FIG. 4 into a calibration bore of known diameter which has known position reflectors such as side drilled holes, flat bottomed holes or round bottomed holes. To obtain the inspection beam surface time during calibration, the inspection beam is bounced off several reflectors such as a reflector 78 in FIG. 4 of known angular and diametrical position. The inspection beam surface time is determined by a non-linear least squares curve fitting method that is discussed in detail in the related patent entitled BORESONIC INSPECTION SYSTEM.

During an inspection, a current ranging surface time $T_r$ is measured using the ranging transducer 70. Since the ultrasonic waves from the ranging transducer 70 and the inspection transducer 72 are incident upon the bore surface 28 at the same circumferential position, differences in the current ranging surface time $T_r$ from the ranging time at calibration $T_{rc}$ can be used to produce the current inspection time $T_i$ from the inspection beam surface time at calibration time $T_{ic}$ in accordance with the following equation:

$$T_i = T_{ic} + (T_r - T_{rc})/\cos q \qquad (3)$$

The angle q is the angle between the ultrasonic beam path of the ranging transducer 70 and the inspection transducer 72, as illustrated in FIG. 4.

Figure 5:
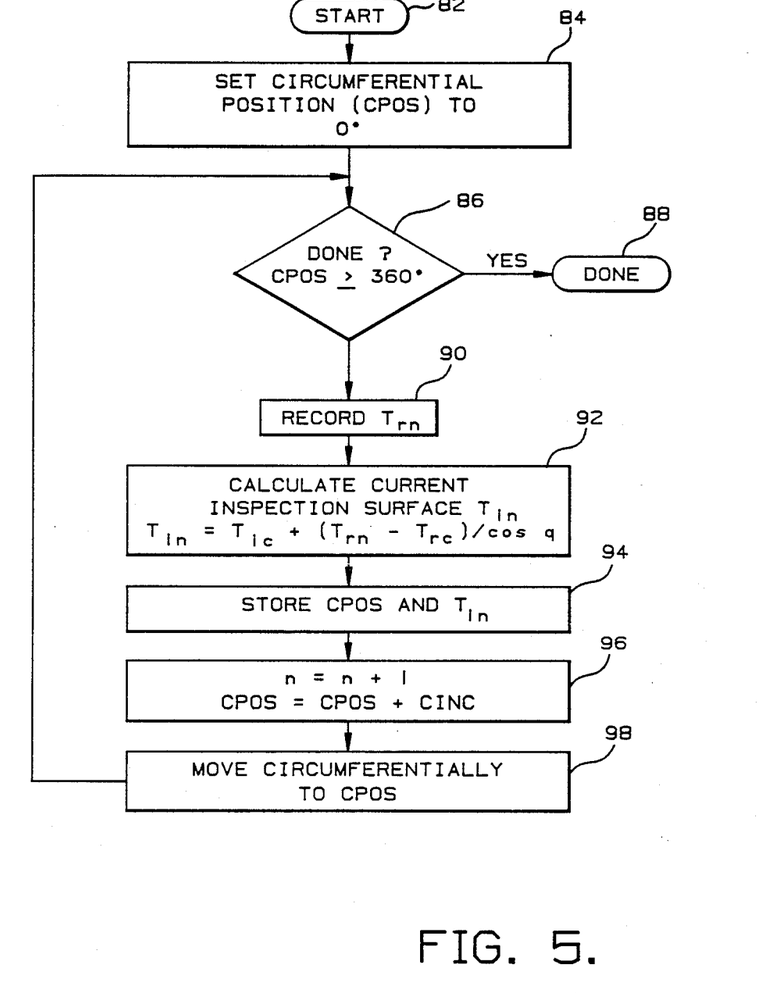
FIG. 5 is a flowchart of a procedure for correcting surface time, for an ultrasonic wave propagating in the rotor in shear mode.

The correction of the surface time for a plurality of points around the circumference of the rotor bore surface can be produced in accordance with the flowchart of FIG. 5. First, the circumferential position CPOS is set 84 to 0°. If the surface time calculation for an entire circuit of the rotor bore surface 28 is completed 86, that is, if the current inspection surface time for an entire 360° rotation has been completed, then the task for the present axial position is complete at 88. If not, the current ranging $T_{rn}$ time is recorded 90. Then the current inspection surface time $T_{in}$ is calculated 92 in accordance with the previously discussed equation. Once the current inspection surface time $T_{in}$ is calculated, it can be stored 94 for later use along with the current circumferential position CPOS. As an alternative, if an inspection pulse is subsequently emitted by the inspection transducer 72, the current inspection time can be used immediately to correct flaw positions. Once the flaw positions are corrected or the corrected surface times are stored, the index n and current position CPOS are updated. The circumferential increment CINC in degrees can be as small as the position resolution of the circumferential drive; however, in practice, the increment is 1.4 degrees. Then the transducer assembly of FIG. 4 is moved to the updated circumferential position at which point the measurement and calculation loop is executed again. Once a complete circuit of the rotor bore has been traversed, it is possible to move the transducer assembly axially and record another set of correction times which can be called a correction time curve.

Figure 6:
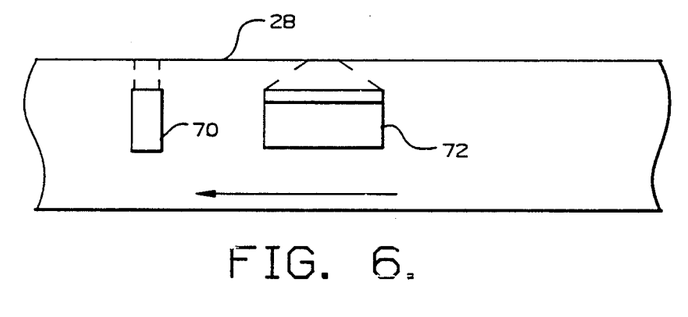
FIGS. 6 and 7 depict axial transducer positions in a surface time measurement system.
Figure 7:
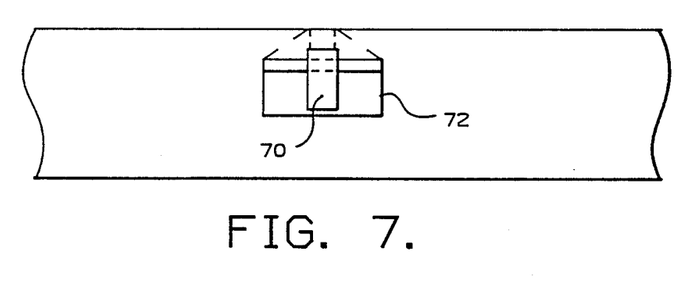

FIG. 6 illustrates the axial relationship of the ranging transducer 70 and inspection transducer 72 as the scan head moves out of the bore in the direction of the arrow to perform an inspection. The distance between the transducers is dictated by the structure of the scan head and is approximately two inches in the preferred scan head. The axial relationship depicted in FIG. 6 is suitable for producing correction curves which are loaded into the flaw gates of the related application to apply the surface correction time to flaw detection positions to correct same. FIG. 7 illustrates the axial relationship of the ranging transducer 70 and inspection transducer 72 when the corrected surface time is used immediately to correct flaw detection locations.

The many features and advantages of the invention are apparent from the detailed specification and thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly, all suitable modifications and equivalents may be resorted to, falling within the scope of the invention. For example, the present invention measures bore diameter at four discrete locations and averages to obtain the mapped diameter. It is possible to circumferentially rotate a single mapping transducer and obtain several hundred diameter measurements which are averaged after completion of the rotation of the mapping transducer assembly. It is also possible to correct the refracted beam path in the inspected object, by using a second order correction, when the surface time is known.

What is claimed is:

1. A bore mapping system, comprising:
    a bore mapping transducer positioned in a bore, producing a transmitted measuring pulse and receiving a reflected measuring pulse; and
    diameter calculation means for calculating a bore diameter from a measured time interval between the transmission of the transmitted measuring pulse and the receipt of the reflected measuring pulse, a calibration time previously measured and a calibration diameter.

2. A system as recited in claim 1, further comprising additional bore mapping transducers and said diameter calculation means calculates a bore diameter for each transducer and calculates an average bore diameter.

3. A system as recited in claim 2, wherein an average bore diameter is calculated for at least two axial positions in the bore.

4. A system as recited in claim 1, wherein an ultrasonic beam produced by said bore mapping transducer is substantially normal to a bore surface at which bore diameter is being measured.

5. A bore mapping system for a turbine rotor, comprising:
    first through fourth ultrasonic transducers immersed in an immersion fluid in the turbine rotor bore each producing a transmitted ultrasonic beam pulse substantially normally incident to a bore surface of the rotor and receiving a reflected beam pulse reflected from the rotor surface; and
    measurement means, coupled to the first through fourth ultrasonic transducers, for measuring the combined ultrasonic travel time $T_s$ of the transmitted and reflected beam pulses of each transducer, calculating a bore diameter D for each transducer in accordance with $D = D_{cal} + V(T_s - T_{cal})$ where $D_{cal}$ is a previously measured calibration diameter, V is the speed of sound in the immersion fluid and $T_{cal}$ is a previously measured calibration travel time between a transmitted beam pulse and a reflected received beam pulse for respective transducers in a calibration bore, averaging the transducer diameters D to produce an average diameter and producing average diameters at different axial positions in the rotor.

6. A bore mapping method, comprising the steps of:
    (a) measuring a calibration diameter and a calibration time in a calibration bore;
    (b) positioning a bore mapping transducer via a spiral movement at a first axial position and a first circumferential position in a mappable bore;
    (c) moving the bore mapping transducer circumferentially to a second circumferential position in the mappable bore offset from the first circumferential position in a plus direction;
    (d) measuring a travel time for a pulse transmitted by the bore mapping transducer, reflected off of a bore surface of the mappable bore and received by the bore mapping transducer;
    (e) producing a measured diameter from the travel time, the calibration time, predetermined pulse travel velocity in an immersion fluid and the calibration diameter;
    (f) positioning the bore mapping transducer via a spiral movement at another axial position and the first circumferential position in the mappable bore; and
    (g) repeating steps (c)-(f) to obtain plural measured diameters measured at plural axial positions.

7. A method as recited in claim 6, wherein step (a) comprises:
    (ai) positioning the bore mapping transducer at an axial position and the first circumferential position in the calibration bore;
    (aii) moving the bore mapping transducer circumferentially in the plus direction to the second circumferential position in the calibration bore;
    (aiii) measuring the travel times as a function of circumferential position for a transmitted pulse to reflect off a calibration bore surface of the calibration bore and be received by the bore mapping transducer;
    (aiv) calculating the calibration time as an average of the measured travel times; and
    (av) mechanically measuring the calibration diameter.

8. A method as recited in claim 6, wherein plural bore mapping transducers are used and step (e) further includes averaging the measured diameters produced with respect to the transducers.

9. A bore mapping method for a turbine rotor containing an immersion fluid, comprising the steps of:
    (a) measuring a calibration diameter mechanically and measuring a first through fourth calibration times in a calibration bore for first through fourth ultrasonic transducers positioned in the calibration bore immersed in the same immersion fluid as contained in the rotor;
    (b) positioning the first through fourth ultrasonic transducers via a spiral movement at a first axial position and a first circumferential position in the rotor bore;
    (c) moving the first through fourth ultrasonic transducers circumferentially to a second circumferential position offset from the first circumferential position in a plus direction;
    (d) measuring first through fourth travel times for a respective pulse transmitted by a respective ultrasonic transducer, reflected off the rotor bore surface at a substantially normal angle and received by the respective ultrasonic transducer;
    (e) producing first through fourth respective measured diameters for respective ultrasonic transducers from the first through fourth travel times, the first through fourth calibration times, a predetermined ultrasonic travel velocity in the immersion fluid and the calibration diameter for the first through fourth ultrasonic transducers;
    (f) averaging the first through fourth measured diameters and storing the averaged diameter and the first axial position as a map segment;
    (g) positioning the first through fourth ultrasonic transducers via a spiral movement at another axial position and the first circumferential position; and
    (h) repeating steps (c)-(g) for plural map segments obtained at plural axial positions.

* * * * *